United States Patent [19]

Tegeler et al.

[11] Patent Number: 4,914,201
[45] Date of Patent: Apr. 3, 1990

[54] INDOLO[1,2-D][1,4]BENZODIAZEPIN-6(7H)-THIONES

[75] Inventors: John J. Tegeler, Bridgewater; Eileen M. Gardenhire, Califon; Grover C. Helsley, Pluckemin, all of N.J.

[73] Assignee: Hoechst-Roussel Pharmaceuticals Inc., Somerville, N.J.

[21] Appl. No.: 428,566

[22] Filed: Oct. 30, 1989

Related U.S. Application Data

[62] Division of Ser. No. 375,444, Jul. 3, 1989.

[51] Int. Cl.⁴ ............................................. C07D 487/04
[52] U.S. Cl. ..................................... 540/494; 540/492
[58] Field of Search ........................................ 540/494

[56] References Cited

U.S. PATENT DOCUMENTS 3,642,779  2/1972  Duncan et al. ...................... 540/494

Primary Examiner—Robert T. Bond
Attorney, Agent, or Firm—Tatsuya Ikeda

[57] ABSTRACT

There are disclosed compounds having the formula

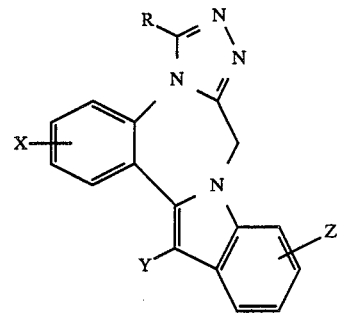

where X is H, halogen, —OH, —OCH$_3$, —NO$_2$ or —CF$_3$; Y is H, Cl or Br; Z is H, halogen, —OH or —OCH$_3$; and R is H, loweralkyl, —CH$_2$OH or diloweralkylaminomethyl, which compounds are useful as analgesic agents.

4 Claims, No Drawings

INDOLO[1,2-D][1,4]BENZODIAZEPIN-6(7H)-THIONES

This is a division of application Ser. No. 375,444, filed July 3, 1989.

The present invention relates to compounds of the formula,

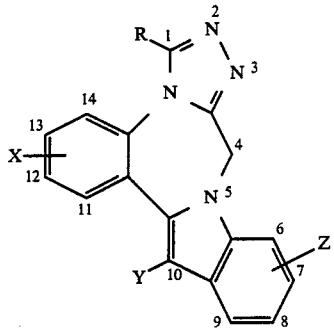

(I)

where X is H, halogen, —OH, —OCH$_3$, —NO$_2$ or —CF$_3$; Y is H, Cl or Br; Z is H, halogen, —OH or —OCH$_3$; and R is H, loweralkyl, —CH$_2$OH or diloweralkylaminomethyl, which compounds are useful as analgesic agents.

The present invention also relates to novel compounds of Formula II which are useful as direct precursors of the target compounds of Formula I.

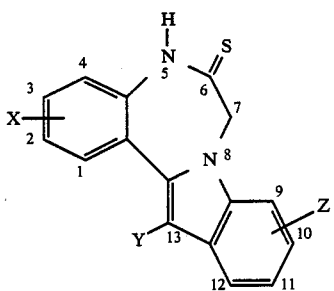

(II)

Unless otherwise stated or indicated, the following definitions shall apply throughout the specification and the appended claims.

The term loweralkyl shall mean a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

The term halogen shall mean fluorine, chlorine, bromine or iodine.

Throughout the specification and the appended claims, a given chemical formula or name shall encompass all stereo, geometrical and optical isomers where such isomers exist.

The compounds of this invention are prepared by utilizing one or more of the steps described below.

Throughout the description of the synthetic steps, the notations, X, Y, Z and R shall have the respective meanings given above unless otherwise stated or indicated, and other notations shall have the respective meanings defined in their first appearances unless otherwise stated or indicated.

STEP A:

A compound of the Formula III is allowed to react with N-chlorosuccinimide (NCS) or N-bromosuccinimide (NBS) in a routine manner known to the art to afford a compound of Formula IV wher Y is Cl or Br, respectively.

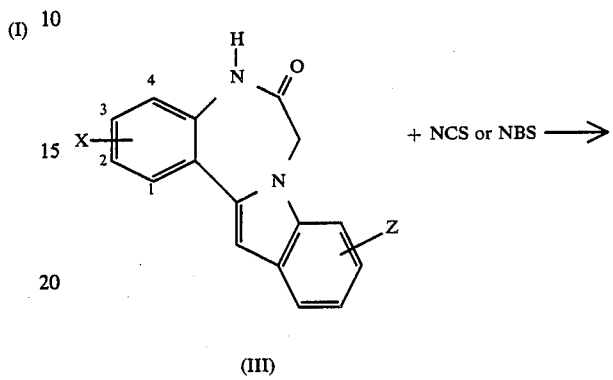

(III)

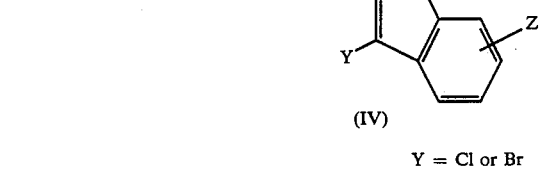

(IV)

Y = Cl or Br

Compounds of Formula III where X is H or 2-Cl as well as a method for their preparation are disclosed in Duncan et al., J. Heterocyclic Chem., Volume 10, 65–70 (1970). Other compounds of Formula III can be prepared by utilizing the method disclosed in the Duncan article.

STEP B:

A compound of Formula V is allowed to react with phosphorus pentasulfide (P$_2$S$_5$) to afford a compound of Formula VI.

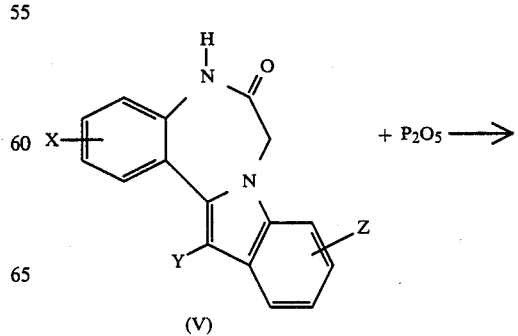

(V)

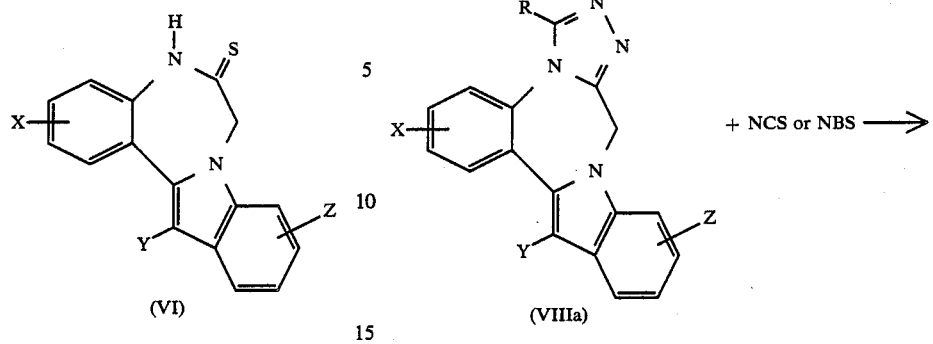

The above reaction is typically conducted in the presence of a mild inorganic base such as sodium or potassium bicarbonate and a suitable solvent such as diglyme at a temperature of about 80° to 160° C.

STEP C:

Compound VI is allowed to react with a hydrazide compound of Formula VII to afford a compound of Formula VIII.

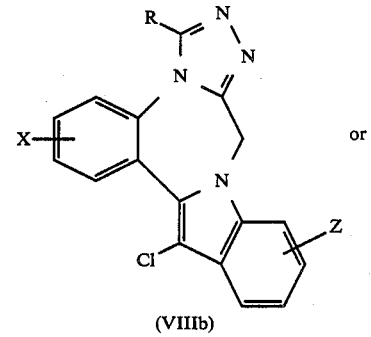

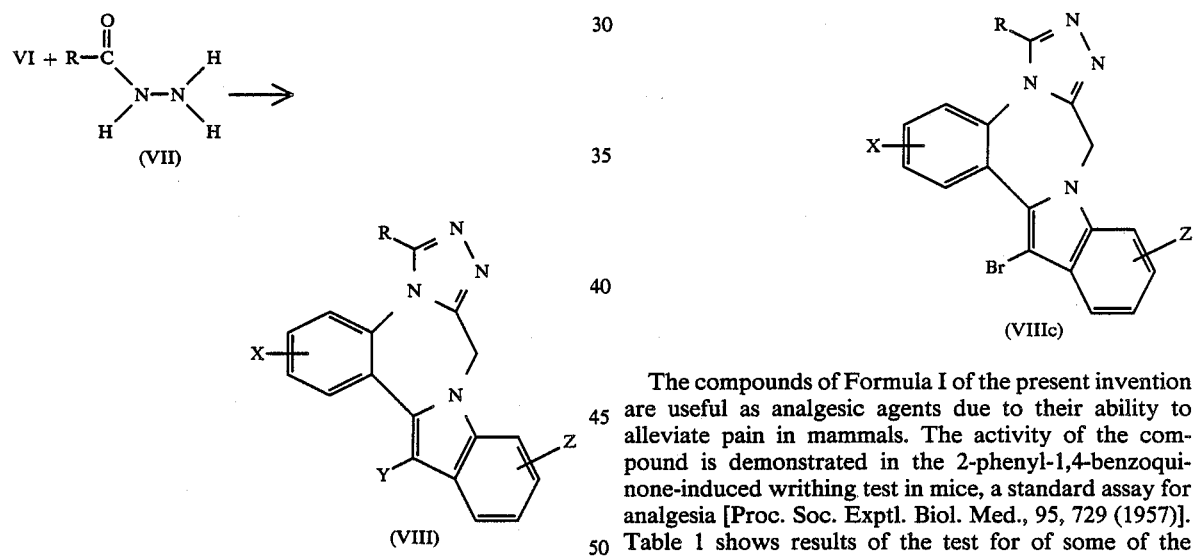

The above reaction is typically conducted in a suitable solvent such as butanol at a temperature of about 60° to 117° C.

STEP D:

As an alternative to the foregoing steps, introduction of Cl or Br into the 10-position of Formula VIII may be accompanied subsequent to the cyclization reaction described as STEP C. Thus, a compound of Formula VIIIa may be allowed to react with N-chlorosuccinimide of N-bromosuccinimide in a routine manner known to the art to afford a compound of Formula VIIIb or VIIIc, respectively, The compounds of Formula I of the present invention are useful as analgesic agents due to their ability to alleviate pain in mammals. The activity of the compound is demonstrated in the 2-phenyl-1,4-benzoquinone-induced writhing test in mice, a standard assay for analgesia [Proc. Soc. Exptl. Biol. Med., 95, 729 (1957)]. Table 1 shows results of the test for of some of the compounds of this invention.

TABLE 1

| Compound | ANALGESIC ACTIVITY (Phenylquinone Writhing) Analgesic PQW, % Inhibition of Writhing at 20 mg/kg., s.c. |
|---|---|
| 12-chloro-1-methyl-4H-indolo-[1,2-d][1,2,4]triazolo[4,3-a]-[1,4]benzodiazepine | 46% |
| 1-methyl-4H-indolo[1,2-d]-[1,2,4]triazolo[4,3-a][1,4]-benzodiazepine | 37% |
| 10,12-dichloro-1-methyl-4H-indolo[1,2,d][1,2,4]-triazolo-[4,3-a][1,4]benzodiazepine | 32% |
| 10-chloro-1-methyl-4H-indolo-[1,2-d][1,2,4]triazolo[4,3-a]-[1,4]benzodiazepine | 51% |

TABLE 1-continued

ANALGESIC ACTIVITY
(Phenylquinone Writhing)

| Compound | Analgesic PQW, % Inhibition of Writhing at 20 mg/kg., s.c. |
|---|---|
| (Reference Compound) Propoxyphene | 50% at 3.9 mg/kg, s.c. |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sufuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweeting agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

Examples of the target compounds of this invention include:

1-Methyl-4H-indolo[1,2-d][1,2,4]triazolo[4,3-a][1,4]benzodiazepine;
10-Chloro-1-methyl-4H-indolo[1,2-d][1,2,4]triazolo[4,3-][1,4]benzodiazepine;
12-Chloro-1-methyl-4H-indolo[1,2-d][1,2,4]triazolo[4,3-a][1,4]benzodiazepine;
10-Bromo-1-methyl-4H-indolo[1,2-d][1,2,4]triazolo[4,3-a][1,4]benzodiazepine;
10,12-Dichloro-1-methyl-4H-indolo[1,2-d][1,2,4]triazolo]4,3-a][1,4]benzodiazepine;
1-(Dimethylamino)methyl-4H-indolo[1,2-d][1,2,4]triazolo[4,3-a][1,4]benzodiazepine;
12-Chloro-1-(dimethylamino)methyl-4H-indolo[1,2-d][1,2,4]triazolo[4,3-][1,4]benzodiazepine;
1-Ethyl-4H-indolo[1,2-d][1,2,4]triazolo[4,3-a][1,4]benzodiazepine;
12-Chloro-1-ethyl-4H-indolo[1,2-d][1,2,4]triazolo[4,3-a][1,4]benzodiazepine;
10,12-Dichloro-1-ethyl-4H-indolo[1,2-d][1,2,4]triazolo[4,3-][1,4]benzodiazepine;
12-Bromo-1-methyl-4H-indolo[1,2-d][1,2,4]triazolo[4,3-a][1,4]benzodiazepine;
12-Chloro-1-hydroxymethyl-4H-indolo[1,2-d][1,2,4]triazolo[4,3-a][1,4]benzodiazepine;
1-Methyl-13-trifluoromethyl-4H-indolo[1,2-d][1,2,4]triazolo[4,3-a][1,4]benzodiazepine;
1-Methyl-12-nitro-4H-indolo[1,2-d][1,2,4]triazolo[4,3-a][1,4]benzodiazepine;
12-Chloro-4H-indolo[1,2-d][1,2,4]triazolo[4,3-a][1,4]benzodiazepine;
12-Methoxy-1-methyl-4H-indolo[1,2-d][1,2,4]triazolo[4,3-a][1,4]benzodiazepine; and
8-Methoxy-1-methyl-4H-indolo[1,2-d][1,2,4]triazolo[4,3-a][1,4]benzodiazepine.

Examples of the direct precursor compounds of this invention include:

Indolo[1,2-d][1,4]benzodiazepin-6(7H)-thione;
13-Chloroindolo[1,2-d][1,4]benzodiazepin-6(7H)-thione; and
2-Chloroindolo[1,2-d][1,4]benzodiazepin-6(7H)-thione.

The following examples are presented in order to illustrate this invention.

EXAMPLE 1

13-Chloroindolo[1,2-d][1,4]benzodiazepin-6(7H)-one

A solution of 1.77 g N-chlorosuccinimide in 50 ml DMF (dimethylformamide) was added dropwise to a mixture of 3.0 g indolo[1,2-d][1,4]benzodiazepin-6(7H)-one in 50 ml dimethylformamide at room temperature. The resulting solution was stirred overnight at room temperature and then poured into 800 ml water. The precipitate was collected, washed with water and dried ($P_2O_5$) under vacuum to give 3.1 g solid, m.p. 287°–289° C.

ANALYSIS: Calculated for $C_{16}H_{11}ClN_2O$: 67.97%C; 3.92%H; 9.91%N. Found: 68.13%C; 4.02%H; 9.94%N.

EXAMPLE 2

13-Bromoindolo[1,2-d][1,4]benzodiazepin-6(7H)-one

A solution of 2.36 g N-bromosuccinimide in 50 ml dimethylformamide was added dropwise to a solution of 3.0 indolo[1,2-d][1,4]benzodiazepin-6(7H)-one in 50 ml dimethylformamide, during which the reaction mixture was cooled with cold water. The resulting solution was stirred at room temperature for two hours and then poured into 800 ml water. The precipitate was collected, washed with water and dried under vacuum (P$_2$O$_5$) to give 3.7 g solid, m.p. 247°–249° C.

ANALYSIS: Calculated for C$_{16}$H$_{11}$BrN$_2$O: 58.73%C; 3.39%H; 8.56%N. Found: 58.94%C; 3.38%H; 8.53%N.

EXAMPLE 3

2,13-Dichloroindolo[1,2-d][1,4]benzodiazepin-6(7H)-one

A solution of 2.08 g N-chlorosuccinimide in 50 ml dimethylformamide was added dropwise at 15° C. to a solution of 4.00 g 2-chloroindolo[1,2-d][1,4]benzodiazepin-6(7H)-one in 125 ml dimethylformamide. The solution was stirred for two hours at room temperature. Upon dilution with water, a solid precipitated, which was collected and washed with hexane. Recrystallization from toluene yielded 2.67 g solid, m.p. 267°–271° C.

ANALYSIS: Calculated for C$_{16}$H$_{10}$Cl$_2$N$_2$O: 60.59%C; 3.18%N; 8.83%N. Found: 60.83%C; 3.25%N; 8.61%N.

EXAMPLE 4

Indolo[1,2-d][1,4]benzodiazepin-6(7H)-thione

A mixture of 15 g indolo[1,2-d][1,4]benzodiazepin-6(7H)-one, 3.09 g phosphorus pentasulfide and 11.46 g sodium bicarbonate in 300 ml diglyme was heated at 100° C. for two hours. The resulting mixture was cooled and poured into 3 L water to precipitate a solid. The solid was collected, triturated successively with cyclohexane, ether and hexane and dried (P$_2$O$_5$) to give 14.1 g solid. Recrystallization of 4.0 g from n-propanol gave 3.0 g solid, m.p. 259°–261° C.

ANALYSIS: Calculated for C$_{16}$H$_{12}$N$_2$S: 72.69%C; 4.58%H; 10.60%N. Found: 72.37%C; 4.48%H; 10.76%N.

EXAMPLE 5

13-Chloroindolo[1,2-d][1,4]benzodiazepin-6(7H)-thione

A mixture of 12.5 g 13-chloroindolo[1,2-d][1,4]benzodiazepin-6(7H)-one, 22.6 g phosphorus pentasulfide and 8.6 g sodium bicarbonate in 240 ml diglyme was heated at 110° C. for two hours. The resulting mixture was cooled and poured into 2.5 L water to precipitate a solid. The solid was collected, washed with water and dried (P$_2$O$_5$) to give 11.9 g crude product. Recrystallization of 3.3 g from toluene (300 ml) gave 2.08 g fluffy solid, m.p. 280°–282° C. (dec.).

ANALYSIS: Calculated for C$_{16}$H$_{11}$ClN$_2$S: 64.31%C; 3.71%H; 9.38%N. Found: 64.56%C; 3.85%H; 9.50%N.

EXAMPLE 6

2-Chloroindolo[1,2-d][1,4]benzodiazepin-6(7H)-thione

A mixture of 3.74 g 2-chloroindolo[1,2-d][1,4]benzodiazepin-6(7H)-one, 2.58 g sodium bicarbonate, and 13.67 g P$_2$S$_5$ in 85 ml diglyme was heated at 105°–120° C. under nitrogen for one and a half hours. The cooled reaction mixtre was diluted with water to precipitate a solid. Recrystallization from toluene yielded 1.58 g solid, which decomposed at 265° C.

ANALYSIS: Calculated for C$_{16}$H$_{11}$ClN$_2$S: 64.32%C; 3.71%H; 9.38%N. Found: 64.18%C; 3.90%H; 9.12%N.

EXAMPLE 7

1-Methyl-4H-indolo[1,2-d][1,2,4]triazolo[4,3-a][1,4]benzodiazepine

A mixture of 6.0 g indolo[1,2-d][1,4]benzodiazepin-6(7H)-thione and 5.08 g acetylhydrazide in 150 ml n-butanol was refluxed under nitrogen for eight hours. Concentration gave a wet residue that was triturated successively with cyclohexane, ether/hexane (1:1), 2-butanone, ether and hexane to give 2.65 g solid. Recrystallization of 2.3 g from water/methanol (2:1) gave 2.2 g solid, m.p. 260°–262° C.

ANALYSIS: Calculated for C$_{18}$H$_{14}$N$_4$: 75.50%C; 4.93%H; 19.57%N. Found: 75.63%C; 5.08%H; 19.56%N.

EXAMPLE 8

10-Chloro-1-menthyl-4H-indolo[1,2d][1,2,4]-triazolo[4,3-a][1,4]benzodiazepine A mixture of 7.8 g 13-chlorindolo[1,2-d][1,4]benzodiazepin-6(7H)-thione and 3.9 g acetylhydrazide in 200 ml n-butanol was refluxed under nitrogen for sixteen hours. Concentration gave a solid residue that was recrystallized from water/methanol (2:3) to give 3.45 g solid, m.p. 282°–285° C.

ANALYSIS: Calculated for C$_{18}$H$_{13}$ClN$_4$: 67.39%; 4.08%H; 17.47%N. Found: 67.35%C; 4.08%H; 17.21%N.

EXAMPLE 9

12-Chloro-1-methyl-4H-indolo[1,2-d][1,2,4]triazolo[4,3-a][1,4]benzodiazepine A mixture of 3.30 g 2-chloroindolo[1,2-d][1,4]benzodiazepin-6(7H)-thione and 1.64 g acetylhydrazide in 85 ml n-butanol was refluxed under nitrogen for sixteen and a half hours. Concentration gave a solid, which was recrystallized from water/methanol to give 2.53 g solid. Purification by flash chromatography using 3% methanal/dichloromethane gave 2.1 g solid, m.p. 249°–253° C.

ANALYSIS: Calculated for C$_{18}$H$_{13}$ClN$_4$: 67.40%C; 4.08%H; 17.47%N. Found: 67.04%C; 4.05%H; 17.28%N.

EXAMPLE 10

10-Bromo-1-methyl-4H-indolo[1,2-d][1,2,4]triazolo[4,3-a][1,4]benzodiazepine

A solution of 2.41 g N-bromosuccinimide in 50 ml dimethylformamide was added dropwise to 3.53 g 1-methyl-4H-indolo[1,2-d[1,2-d][1,2,4]triazolo[4,3-a][1,4]benzodiazepine in 108 ml dimethylformamide. After the addition was complete, the reaction mixture was stirred for one hour at room temperature. Upon addition of water, a solid precipitated, which was collected, washed with water and dried. Recrystallization from water/methanol yielded 2.55 g solid, m.p. 257°–259° C.

ANALYSIS: Calculated for $C_{18}H_{13}BrN_4$: 59.19%C; 3.59%H; 15.34%N. Found: 58.61%C; 3.54%H; 15.10%N.

EXAMPLE 11

10,12-Dichloro-1-methyl-4H-indolo[1,2-d][1,2,4]triazolo[4,3-a][1,4]benzodiazepine A solution of 1.91 g N-chlorosuccinimide in 45 ml dimethylformamide was added dropwise to a solution of 3.33 g 1-methyl-12-chloro-4H-indolo[1,2-d][1,2,4]triazolo[4,3-a][1,4]benzodiazepine in 100 ml dimethylformamide. The reaction mixture was stirred for three hours at room temperature. Upon addition of water and stirring overnight, a solid precipitated. This was collected, triturated with hexane and dried to yield 1.72 g. Recrystallization from methanol/water yielded 1.17 g solid, m.p. 266°-270° C.

ANALYSIS: Calculated for $C_{18}H_{12}Cl_2N_4$: 60.86%C; 3.41%H; 15.77%N. Found: 60.54%C; 3.43%H; 15.49%N.

EXAMPLE 12

1-(Dimethylamino)methyl-4H-indolo[1,2-d][1,2,4]triazolo[4,3-a][1,4]benzodiazepine A mixture of 4.0 g indolo[1,2-d][1,4]benzodiazepin-6(7H)-thione, 2.16 g α-(dimethylamino)acetylhydrazide and 100 ml n-butanol was refluxed under nitrogen for twenty-one hours. Concentration gave an oily solid, which was combined with a similar crude product from a 3.8 mmol scale reaction, and recrystallized from methanol/water to give 3.6 g solid, m.p. 194°-196° C.

ANALYSIS: Calculated for $C_{20}H_{19}N_5$: 72.92%C; 5.81%H; 21.26%N. Found: 72.94%C; 5.81%H; 20.99%N.

EXAMPLE 13

12-Chloro-1-(dimethylamino)methyl-4H-indolo[1,2-d][1,2,4]triazolo[4,3-a][1,4]benzodiazepine A mixture of 5.33 g 2-chloroindolo[1,2d][1,4]benzodiazepin-6(7H)-thione and 4.17 g α-(dimethylamino)acetylhydrazide in 135 ml butanol was refluxed under nitrogen for seventeen hours. Concentration and recrystallization from methanol-water gave a 4.63 g solid, m.p. 233°-236° C.

ANALYSIS: Calculated for $C_{20}H_{18}ClN_5$: 66.02%; 4.99%H; 19.25%N. Found: 65.68%C; 5.06%H; 18.99%N.

We claim:

1. A compound of the formula,

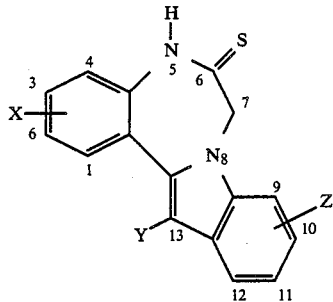

where X is H, halogen, —OH, —OCH$_3$, —NO$_2$ or —CF$_3$; Y is H, Cl or Br; and Z is H, halogen, —OH or —OCH$_3$.

2. The compound as defined in claim 1, which is indolo[1,2-d][1,4]benzodiazepin-6(7H)-thione.

3. The compound as defined in claim 1, which is 13-chloroindolo[1,2-d][1,4]benzodiazepin-6(7H)-thione.

4. The compound as defined in claim 1, which is 2-chloroindolo[1,2-d][1,4]benzodiazepin-6(7H)-thione.

* * * * *